United States Patent
Shimokawa et al.

(10) Patent No.: US 10,182,838 B2
(45) Date of Patent: Jan. 22, 2019

(54) SHOCK WAVE FOCUSING DEVICE, SHOCK WAVE GENERATION APPARATUS, AND SHOCK WAVE ABLATION SYSTEM

(71) Applicant: TOHOKU UNIVERSITY, Sendai-shi Miyagi (JP)

(72) Inventors: Hiroaki Shimokawa, Sendai (JP); Kazuyoshi Takayama, Sendai (JP); Hiroaki Yamamoto, Sendai (JP); Yuhi Hasebe, Sendai (JP); Shokichi Hayasaka, Sendai (JP)

(73) Assignee: TOHOKU UNIVERSITY, Sendai-Shi, Miyagi (JP)

( * ) Notice: Subject to any disclaimer, the term of this patent is extended or adjusted under 35 U.S.C. 154(b) by 321 days.

(21) Appl. No.: 14/655,388

(22) PCT Filed: Dec. 25, 2013

(86) PCT No.: PCT/JP2013/084615
§ 371 (c)(1),
(2) Date: Jun. 25, 2015

(87) PCT Pub. No.: WO2014/104075
PCT Pub. Date: Jul. 3, 2014

(65) Prior Publication Data
US 2015/0359557 A1    Dec. 17, 2015

(30) Foreign Application Priority Data
Dec. 26, 2012  (JP) .................................. 2012-282891

(51) Int. Cl.
*A61B 17/32* (2006.01)
*A61B 17/22* (2006.01)
(Continued)

(52) U.S. Cl.
CPC ...... *A61B 17/320068* (2013.01); *A61B 18/26* (2013.01); *A61N 7/00* (2013.01);
(Continued)

(58) Field of Classification Search
CPC ............ A61B 17/320068; A61B 18/26; A61B 2017/22024; A61B 2017/22025;
(Continued)

(56) References Cited

U.S. PATENT DOCUMENTS 6,203,537 B1    3/2001  Sorin
2002/0183809 A1*  12/2002  Oron .................... A61B 1/0056
607/88
(Continued)

FOREIGN PATENT DOCUMENTS

EP          2630918 A1     8/2013
JP       2004215862    *  8/2004 ............. A61B 17/22
(Continued)

OTHER PUBLICATIONS

Supplementary European Report issued in corresponding European Patent Application No. 13867232, dated Jul. 18, 2016.
(Continued)

*Primary Examiner* — David C Eastwood
*Assistant Examiner* — Vynn Huh
(74) *Attorney, Agent, or Firm* — Browdy and Neimark, P.L.L.C.

(57) ABSTRACT

Provided is a shock wave focusing device for a shock wave ablation system for coagulating and necrosing cardiac muscle tissue that becomes a cause of arrhythmia. A shock wave generation apparatus (10) comprises: a shock wave focusing device (11) which has a concave surface (11*a*); an optical fiber (12) which is inserted into the shock wave focusing device (11); a tubular catheter (13) which guides the optical fiber; an enclosure (14) which constitutes a space
(Continued)

to be filled with liquid at the tip of the optical fiber (12); and the liquid (L) which is filled into the enclosure (14). The shock wave focusing device (11) is configured from a ring-shaped coupling part (16) provided with a central hole (11*b*), and 16 blade parts (17) curved outward from the edge of the coupling part (16) toward the front and provided elastically to the edge of the coupling part (16), and can be folded by rotating the blade parts (17) with respect to the coupling part (16).

13 Claims, 11 Drawing Sheets

(51) Int. Cl.
| | |
|---|---|
| *A61B 18/00* | (2006.01) |
| *A61B 18/26* | (2006.01) |
| *A61N 7/00* | (2006.01) |
| *G02B 6/36* | (2006.01) |
| *G02B 6/26* | (2006.01) |

(52) U.S. Cl.
CPC ............. *G02B 6/262* (2013.01); *G02B 6/36* (2013.01); *A61B 2017/22024* (2013.01); *A61B 2017/22025* (2013.01); *A61B 2018/00351* (2013.01); *A61B 2018/263* (2013.01)

(58) Field of Classification Search
CPC .... A61B 2018/00351; A61B 2018/263; A61N 7/00; G02B 6/262; G02B 6/36
USPC ................................................ 606/2.5; 601/4
See application file for complete search history.

(56) References Cited

U.S. PATENT DOCUMENTS

| | | | |
|---|---|---|---|
| 2003/0013970 A1* | 1/2003 | Makin | A61B 8/12 600/459 |
| 2004/0034380 A1* | 2/2004 | Woolfson | A61F 2/2427 606/170 |
| 2005/0015023 A1* | 1/2005 | Ein-Gal | A61B 17/22004 601/2 |
| 2007/0232913 A1* | 10/2007 | Lau | A61N 7/022 600/439 |
| 2007/0239011 A1 | 10/2007 | Lau et al. | |

FOREIGN PATENT DOCUMENTS

| | | | | |
|---|---|---|---|---|
| JP | 2004215862 A | | 8/2004 | |
| JP | 2004532686 A | | 10/2004 | |
| JP | 2005352268 | * | 12/2005 | ............. G02B 5/00 |
| JP | 2005352268 A | | 12/2005 | |
| JP | 2009061083 | * | 3/2009 | ............. A61B 17/36 |
| JP | 2009061083 A | | 3/2009 | |
| JP | 2009533188 A | | 9/2009 | |
| JP | 2012085812 A | | 5/2012 | |
| WO | 02096501 A2 | | 12/2002 | |

OTHER PUBLICATIONS

Kazuyoshi Takayama et al., "Underwater Shock Wave Focusing by Microexplosions, a Medical Application", The Japan Society of Mechanical Engineers, pp. 119-126, vol. 57, No. 539 (Jul. 1991)—abstract attached.

* cited by examiner

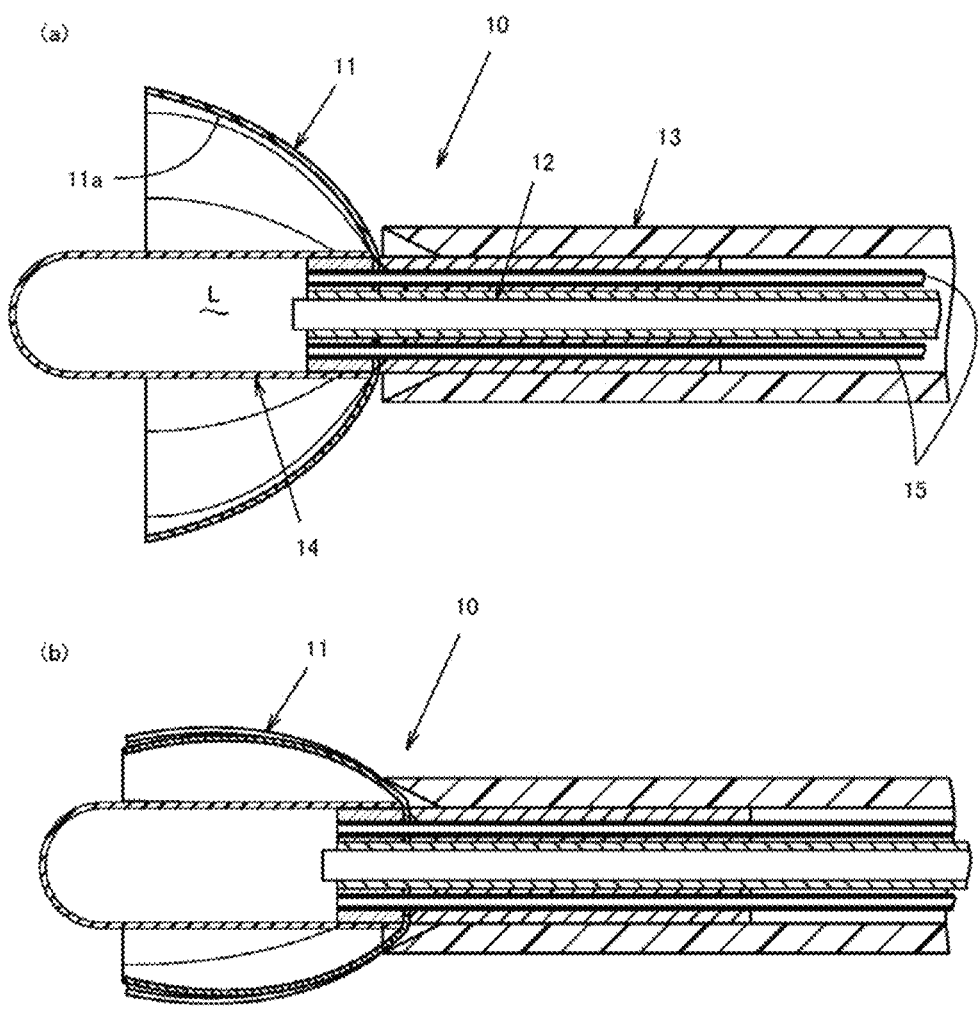
[FIG. 1]

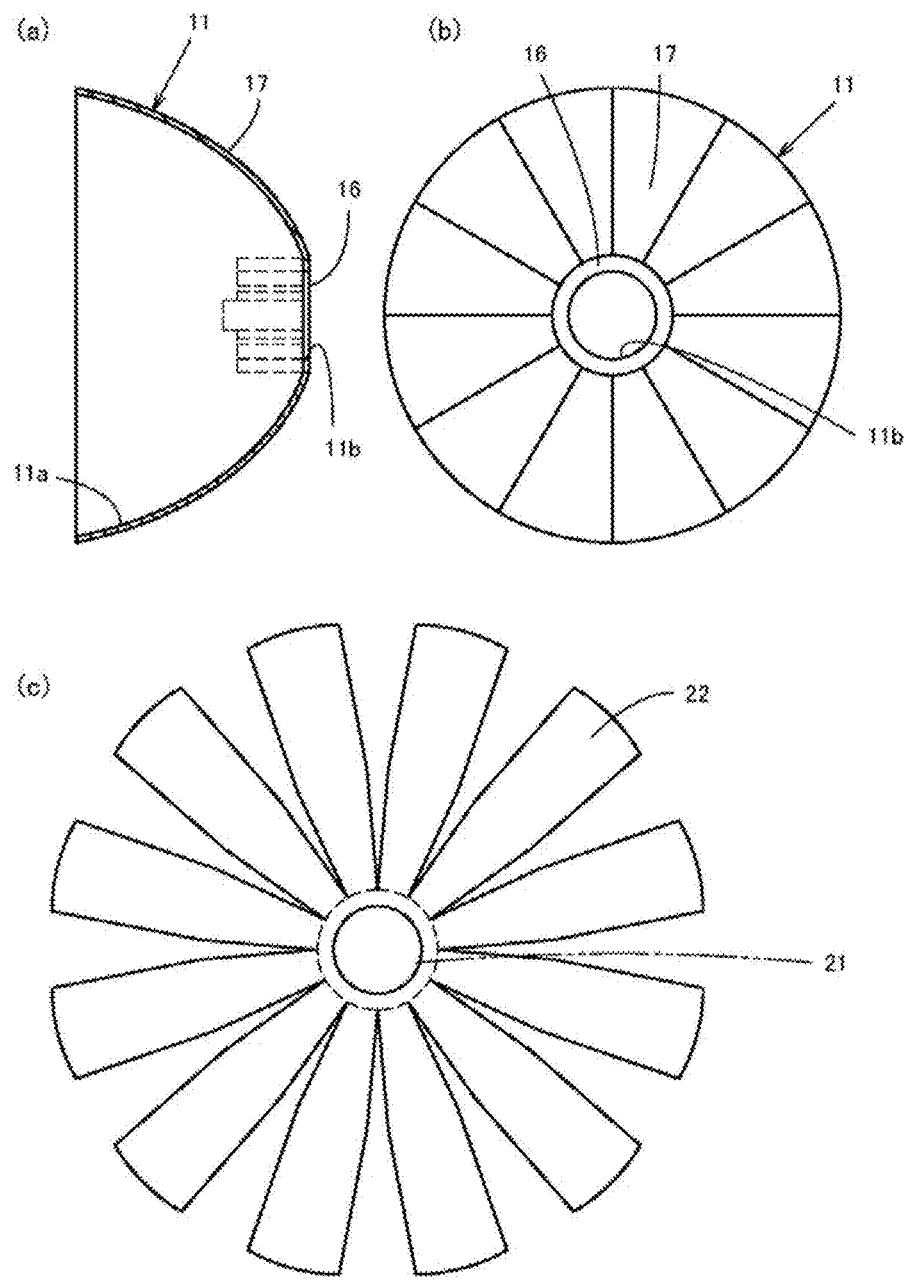
[FIG. 2]

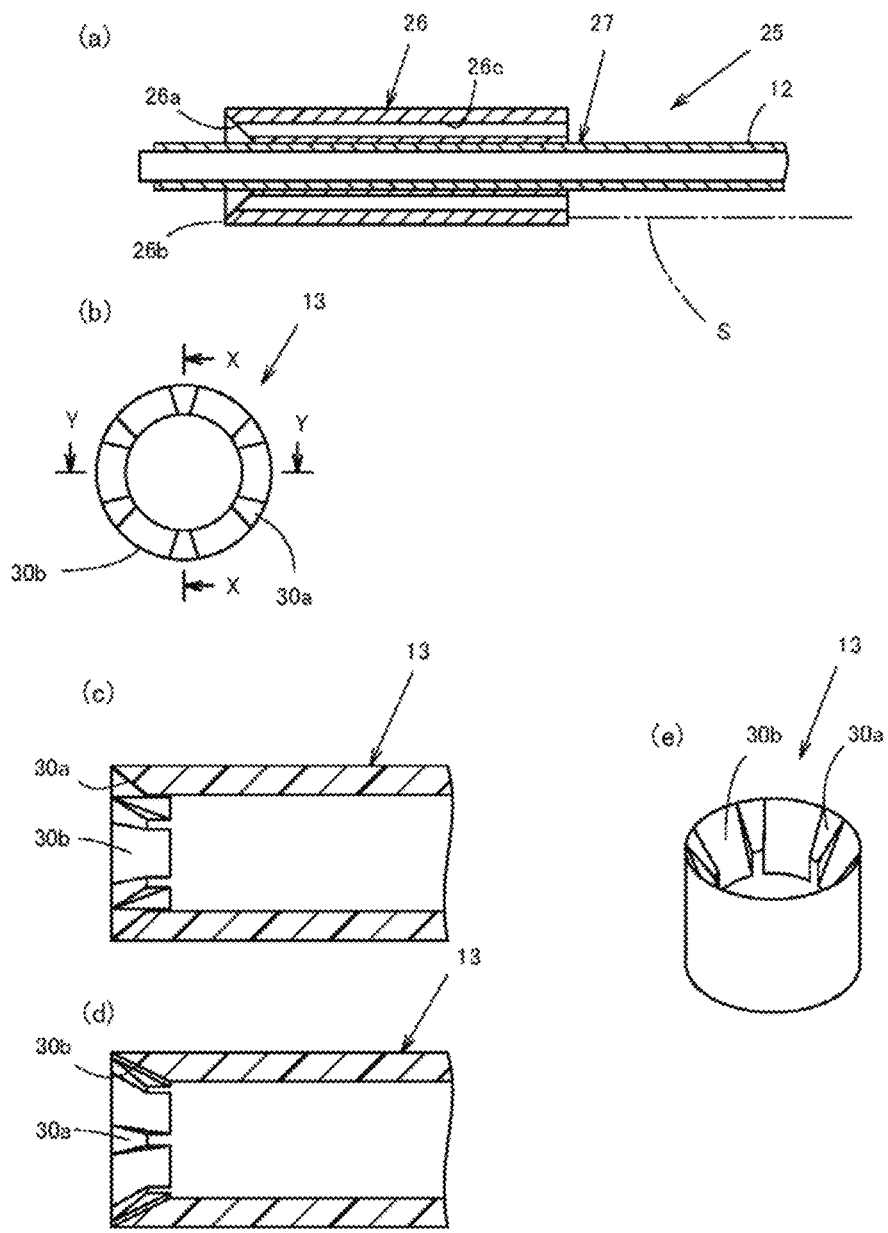
[FIG. 3]

[FIG. 4]
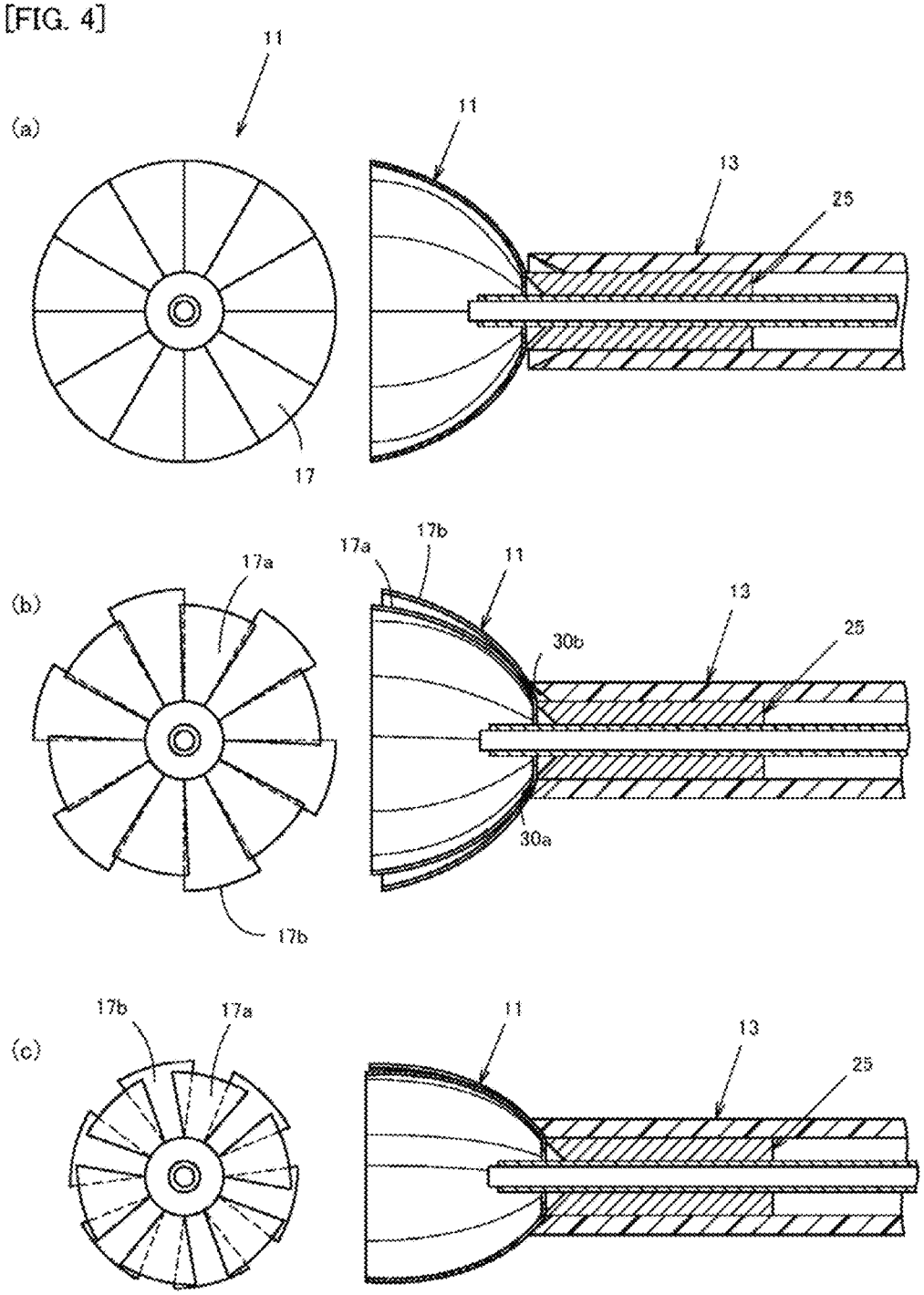

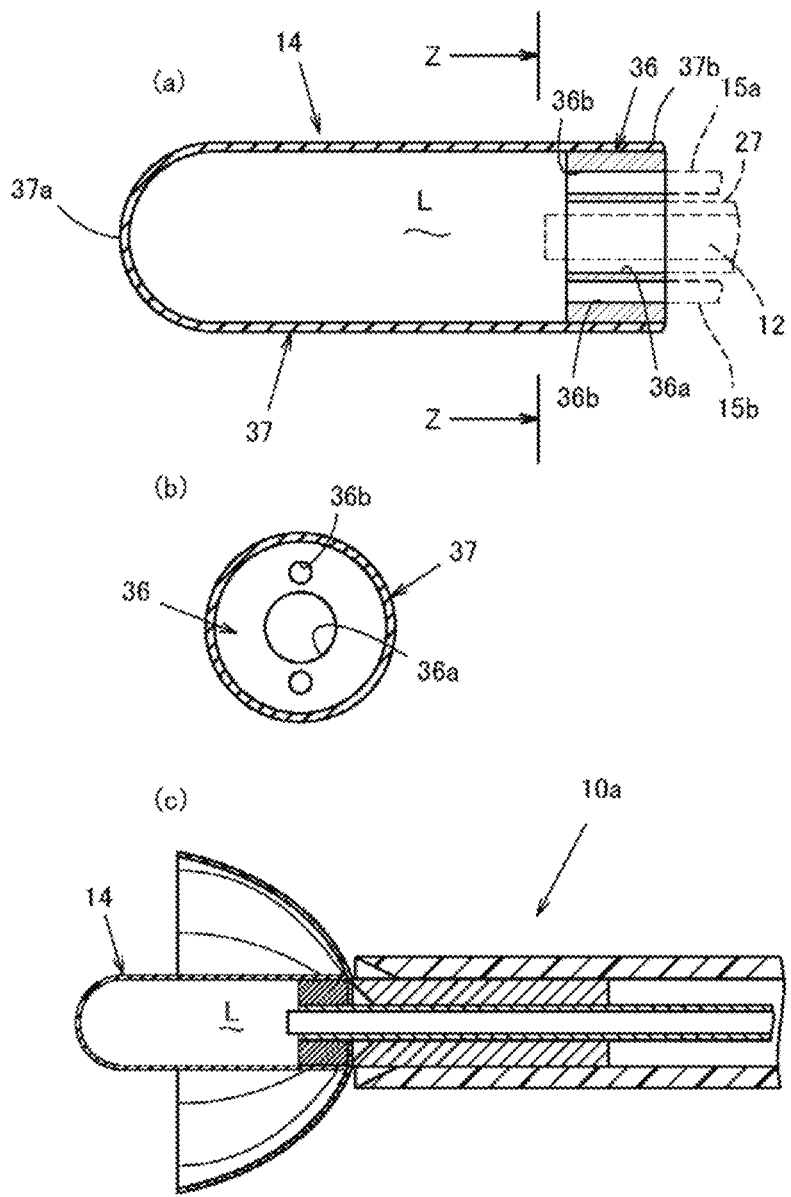

[FIG. 6]
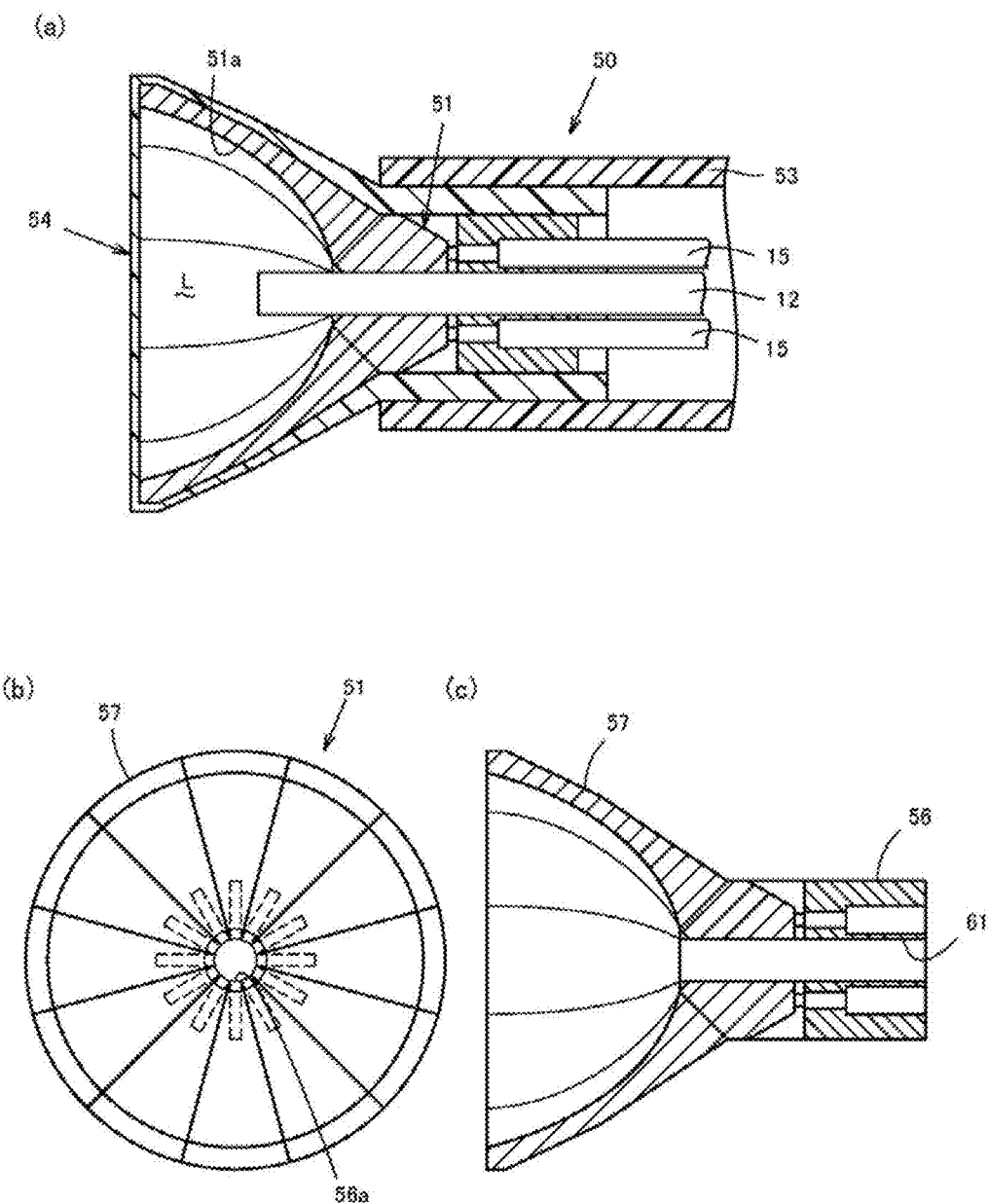

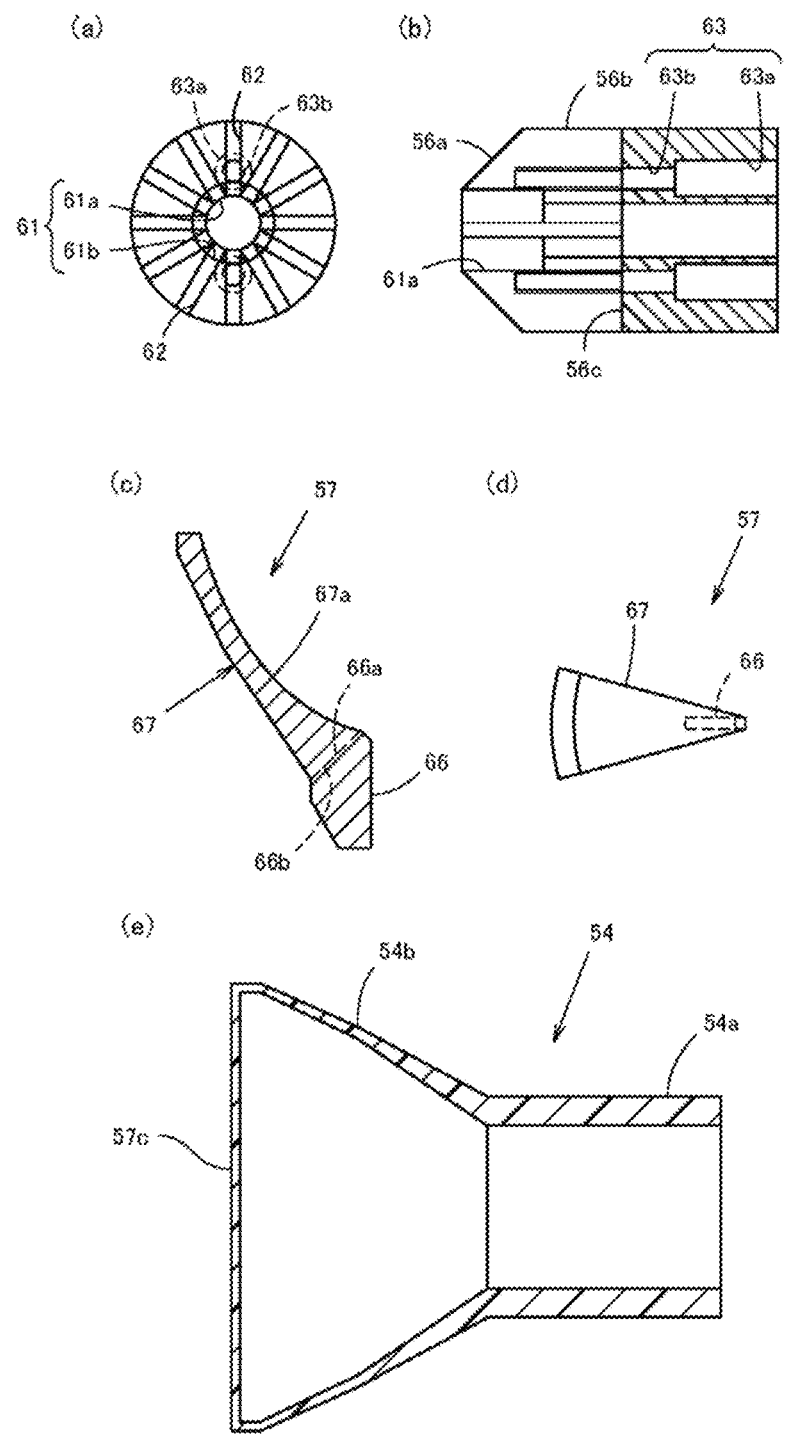
[FIG. 7]

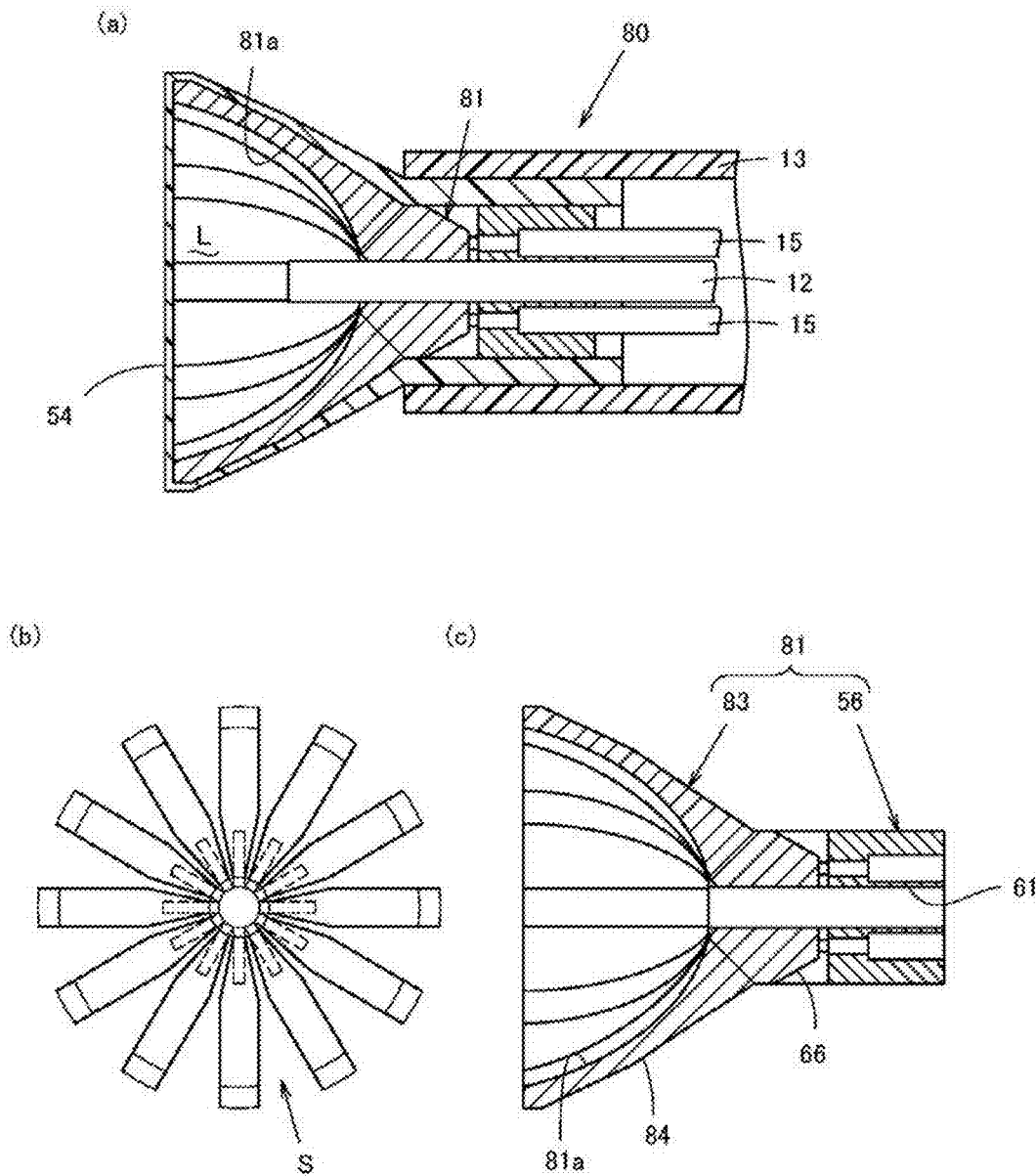

[FIG. 9]
(a)
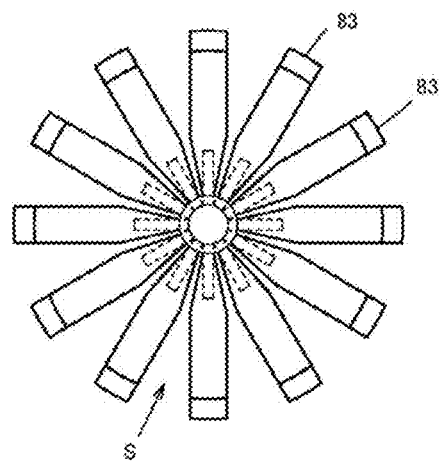 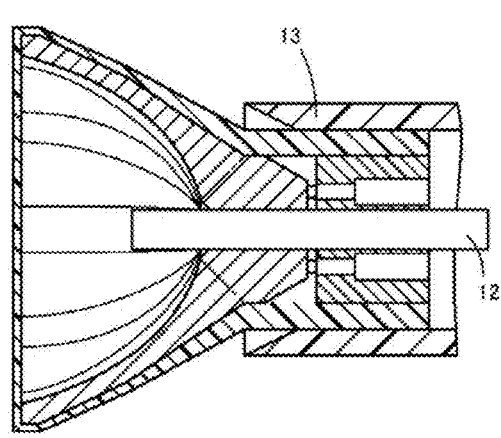
(b)
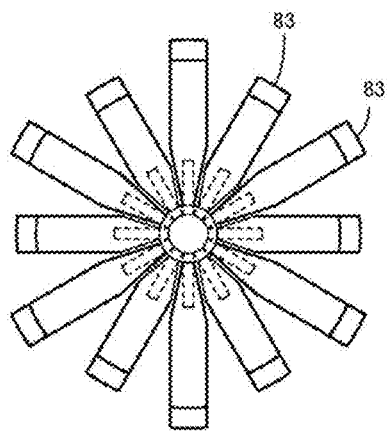 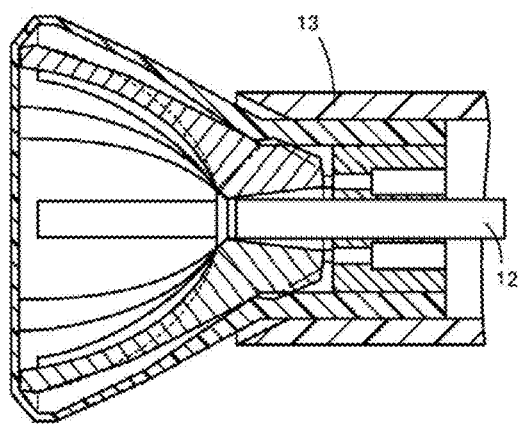
(c)
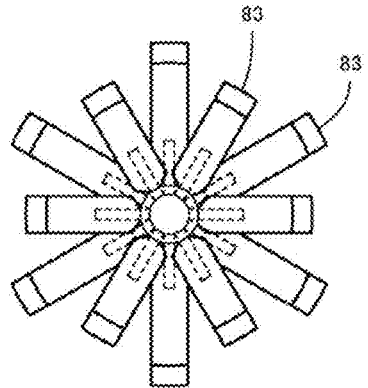 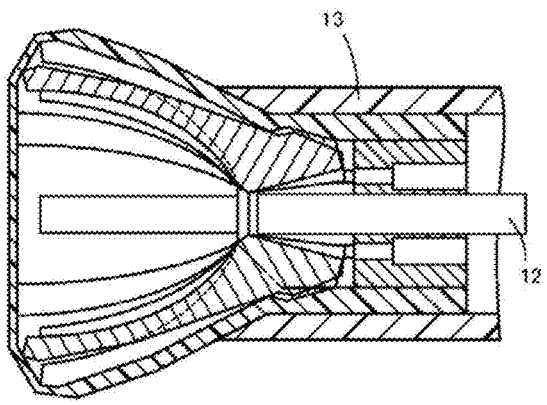

[FIG. 10]
(a)
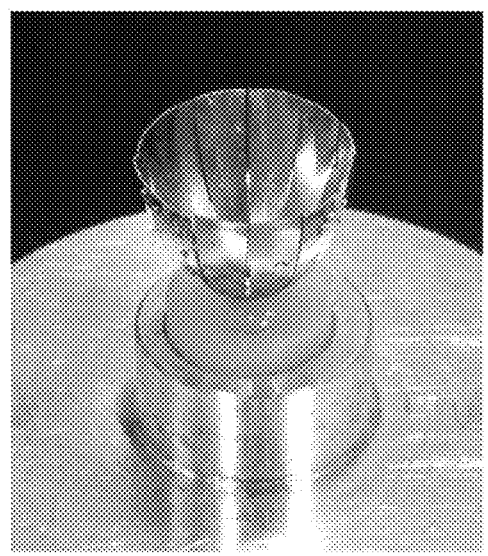
(b)
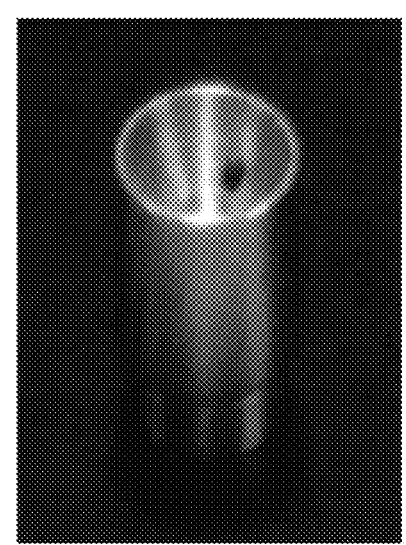

[FIG. 11]
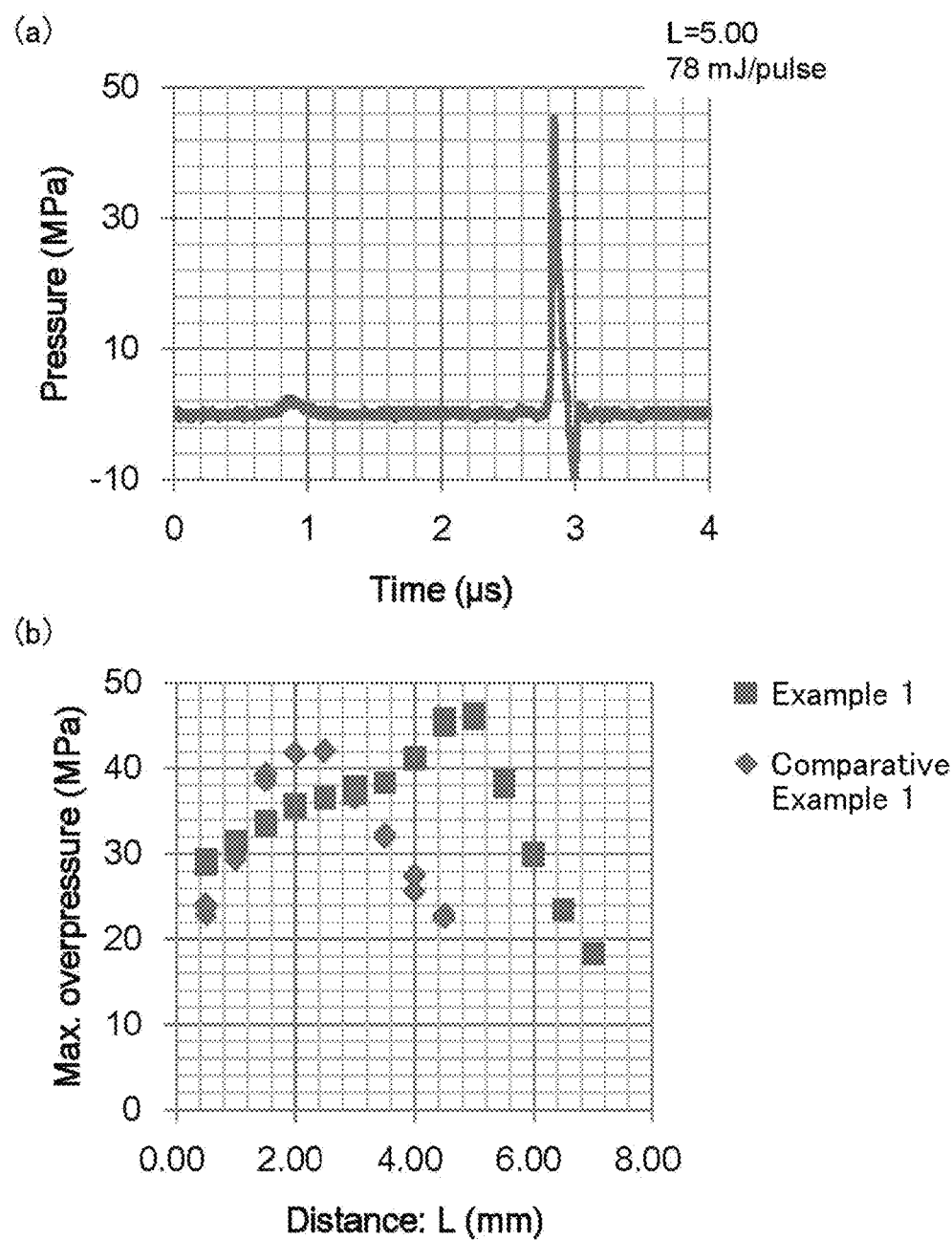

SHOCK WAVE FOCUSING DEVICE, SHOCK WAVE GENERATION APPARATUS, AND SHOCK WAVE ABLATION SYSTEM

FIELD OF INVENTION

The present invention relates to a shock wave focusing device, a shock wave generating device, and a shock wave ablation system.

DESCRIPTION OF BACKGROUND ART

Ablation treatment is introduced and widely prevailed as prevalent technology of non pharmacological treatment for tachyarrhythmia. However, in this treatment, because the treated area is ablated using electrode, it is difficult to treat the source of arrhythmia deep from the surface, and it has a problem that the serious thrombus obstruction may occur in combination with the tachyarrhythmia due to the heat generated by the electrode.

On the other hand, the extracorporeal shock wave lithotripsy (ESWL) to crush and remove the stone in the ureter or kidney by instantaneously forming high pressured area in limited space by focusing the underwater shock wave, is established.

In the non patent document 1, it says that the most efficient ellipticity of rotating ellipsoid to be used as the concave shape of the shock wave focusing device which is to focus the shock wave generated from the point source, is 1.4 to 1.5. It also says that the focusing effect of the shock wave on the outer focal point decreases by increasing the ellipticity. Therefore, it is known to set the ellipticity in less than 2 in view of efficient focusing, and it is known that it is not possible to focus the shock wave beyond 0.87 of the opening diameter of the rotating ellipsoid.

On the other hand, a shock wave reflecting method reflecting the shock wave with the concave surface of the tubular shock wave focusing device is shown in Patent Document 1. This shock wave generating device fixes the shock wave focusing device on tip of the catheter.

PRIOR ART DOCUMENTS

Patent Document

Patent Document 1: Japanese published patent application No. 2009-61083

Non Patent Document

Non Patent Document 1: Transaction of the JSME (in Japanese), Vol. 57, No. 539 (1991-7), No. 90-0920A, P. 119-126

DESCRIPTION OF THE INVENTION

Problems to be Solved

It is known that the shock wave generating device for medical treatment which necrotizes the involved field or lesion which is 5 mm to 10 mm deep from the endocardia (surface), is preferred.

Present applicant downsized the shock wave generating device to be assembled in the catheter and developing the catheter treatment method which presents the damaging effect to the affected area to cure the tachyarrhythmia. However, in the method of the publicly known technology (such as Patent Document 1), the strength of the shock wave strongly decreases when the depth of the lesion passes 3 mm.

The present invention is directed to extend the distance of the focusing point of the shock wave which is to be known as one of most important aspect in the shock wave ablation system of medical treatment and the present invention is directed to provide a shock wave focusing device for shock wave ablation system.

Means of Solving the Problem

A shock wave focusing device for shock wave generating device of the present invention has a shape in which a curved surface rotating body is cut by a flat plane, and has a concave surface with a central hole formed on the axis of the curved surface rotating body for inserting an optical fiber, where a tip of the optical fiber is set on the axis of the curved surface rotating body in a cavity of the concave surface, and where a shock wave which is generated on the tip of the optical fiber is reflected by the concave surface and focused to the outside of the cavity of the concave surface. It is characterized that it comprises a coupling portion provided with the central hole, and blade portions extended radially from the coupling portion and curved outwardly toward a front, where an inner surface of blade portions which is set in a predetermined angle against the center axis of the coupling portion forms the concave surface. The angle between the center axis of the coupling portion and the blade portion is said to be the angle between the tangent line of a rising edge of the blade portion and the center axis of the coupling portion.

In the shock wave focusing device of the present invention, it is preferable that blade portions are rotatably connected to the coupling portion, and when blade portions are set in the predetermined angle against the center axis of the coupling portion the inner surface of the blade portions forms the concave surface, and when blade portions are set in an angle smaller than the predetermined angle against the center axis of the coupling portion the concave surface is folded.

As for the shock wave focusing device of the present invention, the shock wave focusing device in which blade portions are provided on an outer edge of the coupling portion can be cited.

As for the shock wave focusing device of the present invention, the shock wave focusing device in which the coupling portion is tubular body provided with a slit which penetrates from the central hole to the outer edge and which is formed from a front end in a base end direction, in which the blade portions has a blade body configuring the concave surface and a platy support portion extending from a base end of the blade body, and in which the coupling portion and the blade portion are connected by inserting the platy support portion into the slit, can be cited.

In the shock wave focusing device of the present invention, it is preferable that blade portions are connected elastically to the coupling portion. Especially, it is preferable that blade portions are connected elastically in the predetermined angel against the center axis of the coupling portion.

In the shock wave focusing device of the present invention, it is preferable that it further comprises a tubular controlling body which is to insert the optical fiber and which has an inner diameter larger than an outer diameter of the coupling portion, where the blade portions can be folded with the opening of the tubular controlling body by moving the coupling portion against the controlling body to the base direction of the optical fiber.

The present invention of the shock wave generating device is characterized that it is equipped with the shock wave focusing device of the present invention, an optical fiber fixed to the shock wave focusing device, a catheter supporting the optical fiber, an enclosure which constitutes a apace to be filled with liquid at tip of the optical fiber, and the liquid stored in the enclosure. In the shock wave generating device of the present invention, it is preferable that it comprises a liquid supply and drainage device which supplies the liquid to the enclosure and drains the liquid from the enclosure.

The present invention of the shock wave ablation system is characterized that it is equipped with the shock wave generating device of the present invention, a laser oscillator provided on a rear end of the optical fiber.

Effect of the Invention

In the present invention of the shock wave focusing device of the shock wave generating device, because it is equipped with a coupling portion having the central hole, and blade portions which extend radially from the coupling portion and which curve outwardly toward a front, and the inner surface of blade portions which is set in a predetermined angle against the center axis of the coupling portion forms the concave surface, the diameter of the opening of the concave surface can be expanded and the outer focal point of the shock wave can be extended regardless of the diameter of the catheter.

In the present invention of the shock wave focusing device, because blade portions are rotatably connected to the coupling portion, where when blade portions are set in the predetermined angle against the center axis of the coupling portion, the inner surface of the blade portions forms the concave surface, and when blade portions are set in an angle smaller than the predetermined angle against the center axis of the coupling portion, the concave surface is folded, the shock wave focusing device will not be a an obstacle when for forwarding the shock wave generating device into the affected portion of the body.

In the present invention of the shock wave focusing device, because the blade portions are provided on an outer edge of the coupling portion, the structure can be simplified.

In the present invention of the shock wave focusing device, because the coupling portion is tubular body provided with a slit which penetrates from the outer edge and which is formed from a front end in a base end direction, and the blade portions has a blade body configuring the concave surface and a platy support portion extending from a base end of the blade body, and the coupling portion and the blade portion are connected by inserting the platy support portion into the slit, the strength can be increased.

In the present invention of the shock wave focusing device, because blade portions are connected elastically to the coupling portion, the folding operation of the blade portions can be performed easy. Especially, when the blade portions are connected elastically in the predetermined angle against the center axis of the coupling portion, it can be repeatedly use.

Further, in the present invention where the blade portions are elastically connected in the predetermined angle against the center of the coupling portion, because, it further comprises a tubular controlling body which is to insert the optical fiber and which has an inner diameter larger than an outer diameter of the coupling portion, the remote handling of the folding of the blade portions can be easily operated.

In the present invention of the shock wave generating device, because it is equipped with a shock wave focusing device of the present invention, an optical fiber fixed to the shock wave focusing device, a catheter supporting the optical fiber, an enclosure which constitutes a space to be filled with liquid at tip of the optical fiber, and the liquid stored in the enclosure, the outer focal point of the shock wave can be extended regardless of the diameter of the catheter, and the introduction of the shockwave focusing device into the body can be performed easy. Further, when a liquid supply and drainage device which supplies the liquid to the enclosure and drains the liquid from the enclosure is provided, it can wash away the foreign object mixed in the enclosure during the supplying and draining of the liquid. Therefore it can effectively focus the shock wave to the outer focal point.

In the present invention of the shock wave ablation system, because the distance of the focusing point of the shock wave is longer than the conventional one, the treatment of the affected area which is 5 mm to 10 mm deep from the endocardia (surface), is possible, and treatment to the complicated in vivo treatment is possible.

BRIEF DESCRIPTION OF THE DRAWINGS

FIG. 1a is a cross sectional side view showing an embodiment of the shock wave generating device of the present invention, and FIG. 1b is a cross sectional side view showing the shock wave generating device in a condition where the shock wave focusing device is folded.

FIGS. 2a, 2b are a cross sectional side view and a front view showing the shock wave focusing device for the shock wave generating device of FIG. 1; FIG. 2c is a front view of the shock wave focusing device in a condition before pressed.

FIG. 3a is a cross sectional side view showing the support member of the shock wave generating device of FIG. 1; FIGS. 3b, c, d, e are respectively front view, X-X line cross sectional view, Y-Y line cross sectional view, and perspective view of the catheter of the shock wave generating device of FIG. 1.

FIGS. 4a to 4c are cross sectional side views showing the folding process of the shock wave generating device of FIG. 1.

FIG. 5a is a cross sectional view showing the enclosure of the shock wave generating device, FIG. 5b is a Z-Z line cross sectional view; FIG. 5c is a cross sectional side view showing the another embodiment of the shock wave generating device of the present invention.

FIG. 6a is a cross sectional side view showing the other embodiment of the shock wave generating device; FIGS. 6b, c are a front view and a cross sectional side view showing the other embodiment of the shock wave generating device.

FIGS. 7a, b are a front view and a cross sectional view showing the coupling portion of FIG. 6; FIG. 7c, d are a cross sectional view and a front view of the blade portion of FIG. 6; and FIG. 7e is a cross sectional side view of the enclosure of FIG. 6.

FIG. 8a is a cross sectional side view showing the other embodiment of the shock wave generating device; FIGS. 8b, c are a front view and a cross sectional side view showing the other embodiment of the shock wave generating device.

FIGS. 9a to 9c are cross sectional side views showing the folding process of the shock wave generating device of FIG. 1.

FIG. 10a is a photographical view showing example of the shock wave generating device of the present invention; FIG. 10b is a photographical view showing comparative example of the shock wave generating device.

FIG. 11a is a chart showing the shock wave used in test; FIG. 11b is a chart showing the result of the test.

EMBODIMENT FOR CARRYING OUT THE INVENTION

A shock wave generating device 10 of FIG. 1 is equipped with a shock wave focusing device 11 having a concave surface 11a, an optical fiber 12 to be fixed to the shock wave focusing device 11, a catheter 13 guiding the optical fiber 12, an enclosure 14 structuring a space for filling a liquid surrounding the tip of the optical fiber 12, a liquid L charged in the enclosure 14, and a liquid supply and drainage device supplying the liquid to the enclosure and draining the liquid from the enclosure.

The shock wave generating device 10 focuses the shock wave formed in the concave surface 11a which is generated by irradiating the pulse laser to the liquid L in the enclosure 14, to the outside of the cavity of the concave surface 11a by reflecting the shock wave to the concave surface.

A shock wave focusing device 11, like shown in FIGS. 2a, 2b, comprises a coupling portion 16 having a central hole 11b, and twelve blade portions 17 which extend forward from the edge of the coupling portion 16, curved outwardly toward a front, and connected elastically to the edge of the coupling portion 16. That is the blade portion 17 extends radially from the coupling portion 16. In this embodiment, twelve blade portions are used, however the numbers are not limited to this. But, if the number is too large, the gap and the unevenness between the adjacent blade portions will increase and it will increase the loss of the reflection efficiency. On the other hand, if the number is too small, the width of each blade portion need to be enlarged and it will not be favorable for folding. Therefore, the number of the blade portion is preferable to be set from 8 to 16. Further, if the blade portion 17 is folded in two phases as will be discussed later, it is preferable to set the number of the blade portion 17 in even number.

The concave surface 11a is substantially a rotating curved surface formed by rotating a continuous curve which curves outwardly toward the front and projected to the outside. Especially, the curved surface where a spheroid is cut with a flat plane perpendicular to the minor axis or a spheroid is cut with a flat plane perpendicular to the rotating axis, is preferable. By using such a curved surface based on the spheroid the shock wave generated on the focal point in the cavity of the concave surface 11a is reflected by the concave surface 11a and is focused to the outer focal point of the ellipsoidal curved line. It is preferable to have the ellipticity of ellipsoidal curved line (major and minor axis radii ratio) small than 2, especially from 1.4 to 1.8, further from 1.4 to 1.6. By setting the ellipticity below 2, the shock wave generated in the water can be effectively focused to the outer focal point.

The diameter of the opening of the concave surface 11a is set to be larger than the outer diameter of the catheter 13 (see, FIG. 1a). Because the shock wave focusing device 11 can enlarge the opening diameter of the concave surface 11a irrespectively to the diameter of the catheter 13, it can focus the shock wave far from the shock wave focusing device 11. Therefore, the treatment to the affected area which is 5 to 10 mm deep from the endocardia (surface) is possible. The opening diameter of the concave surface 11a can be determined according to the position of the outer focal point (focusing point) and the focusing rate of the shock wave which is to be generated on tip of the optical fiber. It is preferable to set the opening diameter from 2 to 20 mm, more favorable from 4 to 20 mm, further from 2 to 10 mm, most from 5 to 10 mm. Further, the shock wave focusing device 11 can be folded to have the outer diameter of the concave surface 11a to be minimized, therefore, the insertion into the body is easy and the opportunity to treat the affected area inside of the complicated body is increased.

As well the tip of the optical fiber 12 is preferably to be set in the cavity of the concave surface 11a and on the rotating axis of the concave surface 11a. Therefore, the focusing rate of the shock wave which is focused on the outside of the concave surface 11a, can be enhanced. Especially, when the concave surface 11a is rotating ellipsoid and when the tip of the optical fiber is set on the inner focal point of the elliptic curve, the shock wave generated inside the concave surface 11a can be effectively focused at the outer focal point.

The angle of the blade portion 17 against the center axis of the coupling portion (angle between the tangent line of the rising portion and the center axis of the coupling portion) is determined according to the shape of the concave surface 11a. Further, the blade portion 17 is elastically coupled in a predetermined angle to the coupling portion. Therefore, even if the outer force is given to the blade portion 17 and the angle against the coupling portion varies, the angle against the coupling portion recover to the predetermined angle after release of the outer force. However, the blade portion 17 may be elastically connected in an angle larger or smaller to the predetermined angle to the coupling portion. In this case, the concave surface 11a is formed by holding the blade portion 17 at the predetermined angle using a controlling member.

The blade portion 17 is elastically coupled to the edge of the coupling portion 16. Therefore, the blade portion 17 may be deformed such that the angle of the blade portion 17 against the center axis of the coupling portion to be decreased by giving the force to the outer surface of the blade portion 17 in rotating axis direction. That is by giving the force to all of the blade portions 17, the shock wave focusing device will present folded condition like shown in FIG. 4c. Therefore, the outer diameter of the shock wave focusing device may be decreased and the shock wave focusing device 11 itself will not be obstacle when guiding the shock wave focusing device to the affected area in the human body. It is preferable to have the outer diameter of the shock wave focusing device to be folded smaller than the outer diameter of the catheter 13.

The shock wave focusing device 11 is produced by forming a biocompatible metal plate having a ring portion 21 and a radial band 22 extending radially from the edge of the ring portion 21, and curving the radial band 22 by press work to form the blade portion 17. Because, it is produced using the press work, the coupling portion 16 and the blade portion 17 can be coupled with elasticity. It is preferable to use stainless steel for the biocompatible metal.

Further, a metal plate may be adhered to the inner surface of the shock wave focusing device made of plastics or silicone rubber. In this case also, because the shock wave focusing device is integrally formed by plastic or silicone rubber, the coupling portion 16 and the blade portion 17 are elastically coupled.

For the optical fiber 12, conventional one may be used. The shock wave ablation system is structured by connecting the laser oscillator to the base end of the optical fiber 12. For the laser generating device, Q switch laser oscillator can be used, especially Q switch holmium YAG laser can be cited.

In this embodiment, the underwater shock wave is generated by irradiating a pulse laser into the water from the tip of the optical fiber 12. However, the shock wave may be generated by radiating the explosive pellet (for example azide compound such as lead azide, silver azide, etc) which is fixed on tip of the optical fiber 12.

The shock wave focusing device 11 and the optical fiber 12 are connected by a support member 25.

The support member 25, like shown in FIG. 3a, comprises a tubular shock wave focusing device support portion 26 which is fixed on a front end of the shock wave focusing device 11, and a tubular optical fiber support portion 27 fixing the optical fiber by inserting. Further, the optical fiber support portion 27 is inserted in the shock wave focusing device support portion 26 and both are fixed to each other by welding, brazing or with adhesive agent.

The inner surface of the front side of the shock wave focusing device support portion 26 is a tapered surface 26a spreading in front direction and a ringed front end surface 26b is fixed to the rear surface of the coupling portion 16. However, the front side may not be tapered, as long as it can fix the shock wave focusing device. Further, the shock wave focusing device support portion 26 has two penetrating holes 26c penetrating in parallel with the axis. The penetrating hole 26c is a hole which inserts the water supplying pipe 15a and water draining pipe 15b.

The optical fiber support portion 27 covers the outer surface of the optical fiber 12. The optical fiber support portion 27 is a coating body which protects the optical fiber 12 and which is made of rubber or synthetic resin and has flexibility.

For the material of the shock wave focusing device support portion 26 and the optical fiber support portion 27, a hard material having high biocompatible may be used. Especially, stainless steel is preferable.

Because it is structured like above, the shock wave focusing device 11 can be moved back and forth by handling the support member 25 to move back and forth against the catheter 13.

The handling of the support member 25 can be operated by handling the stainless steel line S (imaginary line) which is fixed to the support member 25 and inserted in the catheter 13 like the optical fiber 12, to move back and forth at the base end of the catheter 13.

The catheter 13, like shown in FIGS. 3b to 3e, is equipped with a tubular front edge which has a first tapered surface 30a and a second tapered surface 30b alternately aligned and in which the angles of the first tapered surface 30a and the second tapered surface 30b are different. Both the first tapered surface 30a and the second tapered surface 30b spread in front direction, where the first tapered surface 30a has larger angle. That is, the first tapered surface 30a projected inwardly from the second tapered surface 30b in radial direction. Further, the first tapered surface 30a and the second tapered surface 30b are circularity aligned facing each of the blade portions 17. Therefore, the first tapered surfaces 30a face every other blade portion 17 and the second tapered surfaces 30b face the rest of the blade portion 17. In this embodiment, six surfaces of the first tapered surface 30a and the second tapered surface 30b are formed. Further, the outer diameter of the catheter 13 is determined according to the vessel size to the affected area.

Since the catheter 13 is structured like above, the shock wave focusing device 11 can be fold in two states, like shown in FIG. 4. That is the first tapered surface 30a pushes the outer surface (around the base) of every other blade portion 17a in rotating axis direction by pulling the support member 25 backward against the catheter 13, like shown in FIG. 4b. And the second tapered surface 30b pushes the outer surface (around the base) of the rest of the blade portion 17, by further pulling the support member 25 backward against the catheter 13. Therefore, it can prevent the interference of the adjacent blade portion 17 when folding, and can prevent the deformation of the blade portion 17 due to the interference of the adjacent blade portion 17. In this embodiment, the catheter 13 reacts as the controlling body of the present invention.

The angle of the first tapered surface 30a and the second tapered surface 30b are determined according to the folding rate of the shock wave focusing device. For the material of the catheter 13, flexible synthetic resin, synthetic rubber, etc. can be used.

In this embodiment tapered surface having different angles are used. However, the tapered surface having same angles may be used, and further the tapered surface may be omitted. In this case, the folding of the blade portion 17 is performed in one state.

The enclosure 14, like shown in FIGS. 5a and 5b, is equipped with a columned shaped plug body 36 which fixes the optical fiber 12, the water supplying pipe 15a, and the water draining pipe 15b and which is fixed to the surface of the coupling portion 16, and a cap 37 which is engaged around the plug body 36.

The plug body 36 has a center hole 36a which is formed along the axis and which inserts the optical fiber 12 and the optical fiber support portion 27 and has two lateral holes 36b which are formed along the axis with equal distance from the axis and faces each other across the axis and which inserts the water supplying pipe 15a and the water draining pipe 15b, respectively. The center hole 36a may be formed to only insert the optical fiber 12. The center hole 36a is tightly sealed by inserting the optical fiber 12 and the optical fiber supporting portion 27. The lateral holes 36b are tightly sealed by inserting the water supplying hole 15a and the water draining hole 15b. That is the lateral holes 36b are communicated with the penetrating holes 26c. The synthetic resin material or the rubber material can be used for the plug body 36.

The cap 37 is a tubular body having a round front end 37a and the base 37b engages with the plug body 36. The cap 37 will be tightly sealed by engaging the base 37b to the plug body 36. For the material of the cap 37, a material which can let pass the shock wave is used. Such as, the rubber material especially silicone rubber is preferable. Also, the inside of the cap 37 may be pressurized to have the cap 37 to be blown like a ball.

Because it is structured like above, by charging the liquid L into the sealed space between the plug body 36 and the cap 37, the enclosure 14 will be filled with liquid L.

For the enclosure, a membrane which closes the opening of the concave surface 11a of the shock wave focusing device 11 or a bag which covers the whole of the shock wave focusing device 11 can be used. When using the membrane, the liquid L is supplied into the space between the membrane and the concave surface 11a of the shock wave focusing device 11 by the water supply and drainage apparatus 15.

The water supply and drainage apparatus 15 has the water supplying pipe 15a, the water draining pipe 15b, and the pump (not shown) which is fixed at the base of the water supplying pipe 15a. That is, the liquid L is charged into the enclosure 14 by pump from the water supplying pipe 15a. The base of the water draining pipe 15b may be connected to have circulate the liquid L. By having the water draining pipe 15b, it can sweep away the air bubbles which are formed inside the enclosure or the foreign object which slipped into the enclosure. Therefore, it can prevent the shock wave to reflect on the boundary surface between the air bubble and the water or on the surface of the foreign object. However, like the shock wave generating device 10a shown in FIG. 5c, the water supply and drainage apparatus may be omitted and have the liquid L charged in the enclosure 14.

Next, the operation procedure of the shock wave ablation system using the shock wave generating device 10 is shown. First of all, the shock wave generating device 10 is inserted into the body and is guided to the affected area, in the state where the shock wave focusing device 11 is folded (state of FIG. 4c) by pulling the shock wave focusing device 11 against the catheter in the base end direction. Next, release the shock wave focusing device 11 against the catheter 13 around the affected area and opens the shock wave focusing device (state of FIG. 1 or FIG. 4a). By irradiating the pulse laser at the open state of the shock wave focusing device 11, the shock wave generated at the tip of the optical fiber 12 is then focused to the outer focal point of the concave surface 11a which is the affected area. After the treatment, the shock wave focusing device 11 can again be folded, and the shock wave generating device 10 can be pulled off from the body.

In the shock wave generating device 10, the folding and opening of the shock wave focusing device can be operated under one's hand, the shock wave focusing device 11 won't be an obstacle during the guiding of the shock wave generating device 10, even if the shock wave generating device 10 is guided to the small size vessel around the heart. Further, because the opening diameter of the concave surface 11a of the shock wave focusing device 11 can be enlarged around the affected area, the shock wave can be focused far from the shock wave focusing device 11. Therefore, the affected area which is deep from the surface can be treated. That is, it is especially useful for the shock wave generating device to produce coagulative necrosis of the cardial muscle tissue which is a source of the abnormal cardial rhythm.

In this embodiment, the coupling portion 16 and the blade portions 17 are elastically connected, however it may be connected without elasticity. In this case, the opening and the folding of the shock wave focusing device 11 can be achieved by fixing or interlocking the opening of the catheter (or regulating body) and the blade portion.

Further, the stainless steel line may be fixed to the blade portion 17 of the shock wave focusing device 11 and directly operate the opening and the folding of the shock wave focusing device with the stainless steel line. In this case, it is preferable to have the blade portion 17 to be rotatably connected with the coupling portion 56.

In the shock wave generating device 50 of FIG. 6, the coupling portion and the blade portion are individually formed. Further, the shock wave generating device 50 can not be folded.

The shock wave generating device 50 is equipped with the shock wave focusing device 51 having the concave surface 51a, the optical fiber 12 fixed to the shock wave focusing device 51, the tubular catheter 53 which guides the optical fiber 12, the enclosure 54 which forms the space surrounding the tip of the optical fiber for the liquid to be filled and covers the shock wave focusing device 51, the liquid L charged in the enclosure 54, and the water supply and drainage apparatus 15 which supplies and drains the liquid L into the enclosure. The optical fiber 12 and the water supply and drainage apparatus 15 are substantially same as the one in FIG. 1. Further, the optical fiber 12 may be equipped with the optical fiber support portion 27 like FIG. 1.

The shock wave focusing device 51, like shown in FIG. 6b, 6c, has the tubular coupling portion 56 having the center hole 61, and the blade portion 57 which is applied to the coupling portion 56.

The coupling portion 56, like shown in FIG. 7a, 7b, is a tubular body where the diameter of the front end surface 56a decreases toward the front. It has a plural of slits 62 which penetrates from the center hole 61 to the outer surface 56b and extends from the top to the middle portion 56c. Further, it also has two channels 63 formed from the base end in front direction parallel with the center hole 61.

The center hole 61 comprises the back side center hole 61a which is formed from the base end in the front direction surpassing the middle portion 56c, and the front side center hole 61b formed from the front end of the back side center hole 61a to the top of the center hole 61 and where the diameter is larger than the back side center hole 61a.

Plural slits 62 are formed radially in equal distance. In this embodiment, 12 slits are formed. However, the numbers are not limited as long as the numbers are same as the number of the blade portion.

The channel 63 comprises a tube coupling portion 63a which extends from the base end to just short of the middle portion 56c, and a communicating path 63b which extends from the top of the tube coupling portion 63a to just short of the front end surface 56a of the coupling portion 56 and where the diameter is smaller than the tube coupling portion 63a. The tube coupling portion 63a receives the water supply pipe 15a and the water draining pipe 15b. Two channels 63 is formed facing each other across the center hole 61. The front portion of the communicating path 63b which extends from the middle portion 56c overlaps with the slit 62 (see, FIG. 7a). Therefore, the communicating path 63b which overlaps with the slit 62 communicates both with the front side center hole 61b of the center hole 61 and the slit 62.

Two channels 63 are to supply and drain the liquid L to the concave surface 51a. The supply route of the liquid L to the concave surface 51a is from the supply pipe 15a which is connected to the base end of the channel 63 to the front side center hole 61b of the center hole 61 through the slit 62, and to the concave surface 51a. On the other hand the drain route of the liquid is from the back side center hole 61a of the center hole 61 to the channel 63 through the slit 62 and to the water draining pipe 15b connected to the base end of the channel 63.

The blade portion 57, shown in FIG. 7c, 7d, has a platy supporting portion 66, and a platy blade piece 67 which is curved and which extends forward from the top of the supporting portion. The surface of the support portion 66 and the surface of the blade piece 67 are substantially perpendicular to each other. The surface of the support portion 66 extends from the surface of the blade piece 67.

The support portion 66 is to be inserted into the slit 62 of the coupling portion, the front end surface 66a of the front end 56a of the coupling portion is to have same angle. The thickness of the support portion 66 is structure to be as same as the width of the slit 62 or smaller.

The blade piece 67 has a width that is lager than the thickness of the support portion 66 and has a platy body which curved outwardly. The inner surface 67a of the blade piece 67a forms a rotating curved surface which extends from the edge (around the long axis) of the center hole of the coupling portion. This inner surface forms the concave surface 51a. The back end surface 67b in the length direction of the blade piece 67 declined so as to engages with the front end surface of the coupling portion 56 in the length direction. That is the back end surface 67b is supported by the front end surface of the coupling portion when the supporting portion 66 of the blade portion 57 is inserted in the slit 62. The width of the blade piece 67 is structured, so that the inner surface of the adjacent blade pieces are tightly arranged when the adjacent blade portions 57 are inserted in the slit 62 to form the concave surface 51a. That is, the width is determined according to the number of the blade pieces 67 and the width of the blade pieces.

The concave surface 51a which is structured by the blade pieces 67 is rotating curved surface substantially same as the concave surface 11a of FIG. 1, and the diameter of the opening is larger than the outer diameter of the coupling portion 56. And it is also larger than the outer diameter of the catheter 53.

The thickness of the blade piece 67 is set between 0.4 mm to 1 mm, especially between 0.3 mm to 0.5 mm. By applying the thickness to the blade piece 67, the thickness can be applied to the concave surface 51a, therefore it can enhance the durability of the shock wave focusing device 51 and enables the downsizing.

Because it is structured like above, the opening of the concave surface can be enlarged and the distance of the focusing point of the shock wave can be extended regardless of the diameter of the catheter.

The catheter 53 is a tubular body which covers the shock wave focusing device 51 and the enclosure 54. The outer diameter of the catheter is determined according to the diameter of the vessel to the affected area.

The enclosure 54, like shown in FIG. 7e, is a cap which covers the coupling portion 56 and the blade portion 57. The enclosure 54 comprises a tubular portion 54a which covers the coupling portion 56, and a cover portion 54b which is formed on top of the tubular portion 54a. The enclosure 54 has a truncated cone shape, and covers the blade portion 57. The cover portion 54b has a front edge face 54c. The enclosure 54 is preferably made to be flexible cap.

The shock wave generating device 50 has high durability because it is equipped with the shock wave focusing device 51.

To operate the shock wave ablation system using the shock wave generating device 50, the shock wave focusing device 51 is fixed on top of the catheter, then the shock wave focusing device 51 is inserted into the heart via the vessel, and the front end of the shock wave focusing device 51 is perpendicularly contacted to the affected area. And the shock wave is focused to the affected area by irradiating the pulse laser from the tip of the optical fiber. It is preferably to set the outer diameter from 2 to 6 mm, especially from 2 to 5 mm, when the shock wave focusing device 51 is used for the inside of the heart. It is because, when the outer diameter is larger than 6 mm it prevents the shock wave focusing device 51 to be inserted from the vessels near the heart, and when the outer diameter is smaller than 2 mm the distance of the focusing point will not be enough.

Further the shock wave focusing device 51 may be used for other shock wave irradiated treatment of the other body portion other than the heart. For example, when it is used for calculus fragmentation or such, the shock wave focusing device 51 may be inserted into the body during the endoscope or abdominoscope. In this case, the outer diameter of the shock wave focusing device 51 is preferably to be set from 2 to 20 mm, especially from 2 to 10 mm. It is because, when the outer diameter is larger than 20 mm it prevents the shock wave focusing device 51 to be inserted from the endoscope or abdominoscope, and when the outer diameter is smaller than 2 mm the distance of the focusing point will not be enough.

The shock wave generating device 80 is another embodiment in which the coupling portion and the blade portion are formed apart and connected afterwards and the blade portion is foldable.

The shock wave generating device 80 is equipped with the shock wave focusing device 61 having the concave surface 81a. It is also equipped with the optical fiber 12, the catheter 13, the enclosure 54, the liquid L, and the water supply and drainage device 15. The optical fiber 12, the catheter 13, the liquid L, and the water supply and drainage device 15 are substantially same as those of the shock wave generating device 10 in FIG. 1, and the enclosure 54 is substantially same as one of the shock wave generating device 50 in FIG. 6. Further, the enclosure 54 has a flexibility which can deform according to the folding of the blade portion and it is made from the natural rubbers, the synthetic rubbers, or the synthetic resins.

The shock wave focusing device 81, like shown in FIGS. 8b, 8c, comprises a tubular coupling portion 56 having a center hole 61, and a blade portion 83 which is connected to the blade portion 56. The coupling portion 56 is substantially same as the coupling portion 56 of FIG. 6.

The blade portion 83 has a thin supporting portion 66, and a blade piece 84 which is curved and which extends with curved shape from the top of the supporting portion. The supporting portion 66 is substantially same as the supporting portion 66 of FIG. 7.

The thickness of the blade piece 84 is structured so that when the adjacent blade portion 83 is inserted in the slit 62, the space S is formed between the thickness direction of the inner surface of two adjacent blade pieces. That is, the concave 81a structured with the blade pieces 84 has plural of spaces S extending in a radial fashion. The other configuration is substantially same as the blade piece 67 of FIG. 6 and has the back end surface 67a. And the thickness of the blade piece 67 is formed from 0.04 to 1 mm, especially from 0.3 to 0.5 mm. Therefore, the depth is added to the concave surface 81a, in another word the strength is given to the concave surface 81a, the durability of the shock wave focusing device 81 is enhanced, and the downsizing is possible. Further, the opening diameter of the concave surface 81a is larger than the outer diameter of the catheter 13.

Next, the folding operation of the shock wave focusing device 81 is shown. First, like shown in FIG. 9a, the blade piece 67 of the blade portion 83 is closed by the catheter 13. The optical fiber 12 is inserted in the center hole 61 of the coupling portion 56 so as the tip of the optical fiber 12 is set in the coupling portion 56 of the shock wave focusing device 81. Then the optical fiber 12 is pushed so that the tip of the optical fiber 12 is pushed out to the focal point of the elliptic curve of the concave surface 81a from the inside of the center hole 61 of the coupling portion 56. Hereby, the lateral face of the optical fiber support portion 27 push the inner surface of the blade piece 84 of the blade portion 83 in thickness direction, and the blade piece opens. That is the closing operation of the shock wave focusing device 81 is performed by the catheter 13 and the opening operation of the shock wave focusing device 81 is performed by the optical fiber 12.

Because the concave surface 81a has thickness and the concave surface 81a has radially extending space S, the shock wave focusing device 81 has high durability and foldable. That is the supporting portion 66 of the blade portion 83 can rotate in the slit 62 by narrowing or closing the gap S and can minimize the diameter of the circle connecting the tip of the blade piece 84.

EXAMPLE

Example 1

The shock wave focusing device 11 in which the ellipticity is 1.41, the opening diameter of the shock wave focusing device 11 is 7.8 mm, is formed by the cutting the thin plate of stainless steel (0.1 mm) like shown in FIG. 2*c* and press work (see, FIG. 10*a*). The outer diameter when in folded state is 3.66 mm. This shock wave focusing device 11 is example 1.

Comparative Example 1

The shock wave focusing device in which the ellipticity is 1.6, the opening diameter of the shock wave focusing device is 3.6 mm, is formed from the column shaped brass by cutting operation to form the concave surface (see, FIG. 10*b*). This shock wave focusing device made of brass is comparative example.

The shock waves were generated on the inner focal point of the shock wave focusing device of example 1 and comparative example 1. And the focused shock waves were measured at the outside of the shock wave focusing device. The results are shown in FIG. 11*b*.

As seen in the result of the FIG. 11*b*, the distance of the focusing point from the shock wave focusing device of example 1 is longer than the distance of the focusing point from the shock wave focusing device of comparative example 1. Further, the maximum excessive pressure of the shock wave of example 1 is larger than the maximum excessive pressure of the shock wave of comparative example 1. Especially when the shock wave focusing device of example 1 is used, the focusing point was extended for 5 mm. And it became known that this device can irradiate the focused shock wave to the area of 5 to 10 mm depth from the endocardia (surface) which is preferably known for the treatment of arrhythmia. Further, it became known that the shock wave focusing device of example 1 can generate the shock wave in which the maximum excessive pressure is 45 MPa.

The invention claimed is:

1. A shock wave focusing device for a shock wave generating device, comprising:
a coupling portion provided with a central hole and having a center axis, a plurality of blade portions extended radially from the coupling portion and curved outwardly toward a distal end of the plurality of blade portions, and an optical fiber,
wherein an inner surface of the blade portions which is set in a predetermined angle relative to the center axis of the coupling portion forms a distally facing concave surface,
the concave surface having a shape that is rotationally symmetric about the center axis and having a central hole formed on the center axis for insertion of the optical fiber, a tip of the optical fiber being set on the central axis in a cavity of the concave surface so as to enable a shock wave generated on the tip of the optical fiber to be reflected by the concave surface and focused outside of the cavity of the concave surface, and further comprising an enclosure that encloses a space, distinct from the cavity defined by the concave surface, the enclosure filled with liquid at the tip of the optical fiber, the enclosure extending distally beyond the distal end of the blade portions.

2. The shock wave focusing device according to claim 1, wherein the blade portions are connected to the coupling portion symmetrically about the center axis, and
the blade portions being coupled to the coupling portion so as to enable the blade portions to be set in the predetermined angle relative to the center axis of the coupling portion and to be set in an angle smaller than the predetermined angle relative to the center axis of the coupling portion, such that when the blade portions are set in the predetermined angle relative to the center axis of the coupling portion, the inner surface of the blade portions forms the concave surface, and when the blade portions are set in an angle smaller than the predetermined angle relative to the center axis of the coupling portion, the concave surface is folded.

3. The shock wave focusing device according to claim 2, wherein the blade portions are integrally formed with the coupling portion.

4. The shock wave focusing device according to claim 3, wherein the blade portions are integrally formed in the predetermined angle relative to the center axis of the coupling portion.

5. The shock wave focusing device according to claim 2, further comprising a tubular controlling body which is to insert the optical fiber and which has an inner diameter larger than an outer diameter of the coupling portion, wherein the blade portions are slidable into a central hole of the tubular controlling body that folds the blade portions, by the coupling portion being slidable into the central hole of the tubular controlling body toward a proximal end of the tubular controlling body.

6. The shock wave focusing device according to claim 2, wherein the blade portions are provided on an outer edge of the coupling portion.

7. The shock wave focusing device according to claim 2, wherein the coupling portion is a tubular body provided with a slit which penetrates from the central hole to an outer edge and which is formed from a distal end of the tubular body in a proximal end direction, wherein the blade portions has a blade body configuring the concave surface and a platy support portion extending from a proximal end of the blade body, wherein the coupling portion and the blade portion are connected by inserting the platy support portion into the slit.

8. The shock wave focusing device according to claim 1, wherein the blade portions are provided on an outer edge of the coupling portion.

9. The shock wave focusing device according to claim 1, wherein the coupling portion is a tubular body provided with a slit which penetrates from the central hole to an outer edge and which is formed from a distal end of the tubular body in a proximal end direction, wherein the blade portions has a blade body configuring the concave surface and a platy support portion extending from a proximal end of the blade body, and wherein the coupling portion and the blade portion are connected by inserting the platy support portion into the slit.

10. A shock wave generating device comprising:
the shock wave focusing device of claim 1, the optical fiber being fixed to the shock wave focusing device, and
a catheter supporting the optical fiber.

11. The shock wave generating device according to claim 10, further comprising a liquid supply and drainage device which supplies the liquid to the enclosure and drains the liquid from the enclosure.

12. A shock wave ablation system, comprising:
the shock wave generating device according to claim 10,
a laser oscillator provided on a proximal end of the optical fiber.

13. A shock wave focusing device for a shock wave generating device, comprising:
a coupling portion provided with a central hole and having a center axis, a plurality of blade portions extended radially from the coupling portion and curved outwardly toward a distal end of the plurality of blade portions, and an optical fiber,
wherein an inner surface of the blade portions which is set in a predetermined angle relative to the center axis of the coupling portion forms a distally facing concave surface,
the concave surface having a shape that is rotationally symmetric about the center axis and having a central hole formed on the center axis for insertion of the optical fiber, a tip of the optical fiber being set on the central axis in a cavity of the concave surface so as to enable a shock wave generated on the tip of the optical fiber to be reflected by the concave surface and focused outside of the cavity of the concave surface, and
further comprising an enclosure that encloses a space, distinct from the cavity defined by the concave surface, the enclosure filled with liquid at the tip of the optical fiber,
wherein the blade portions are connected to the coupling portion symmetrically about the center axis, and
wherein the blade portions are coupled to the coupling portion so as to enable the blade portions to be set in the predetermined angle relative to the center axis of the coupling portion and to be set in an angle smaller than the predetermined angle relative to the center axis of the coupling portion, such that when the blade portions are set in the predetermined angle relative to the center axis of the coupling portion, the inner surface of the blade portions forms the concave surface, and when the blade portions are set in an angle smaller than the predetermined angle relative to the center axis of the coupling portion, the concave surface is folded.

* * * * *